United States Patent [19]

Rizkalla

[11] Patent Number: 4,618,705
[45] Date of Patent: Oct. 21, 1986

[54] PROCESS FOR CONVERSION OF ACID ANHYDRIDES TO ALKYLIDENE DIESTERS

[75] Inventor: Nabil Rizkalla, River Vale, N.J.

[73] Assignee: The Halcon SD Group, Inc., Montvale, N.J.

[21] Appl. No.: 341,977

[22] Filed: Jan. 22, 1982

Related U.S. Application Data

[63] Continuation of Ser. No. 171,064, Jul. 22, 1980, abandoned.

[51] Int. Cl.$^4$ .................... C07C 67/00; C07C 69/003; C07C 69/007; C07C 69/16
[52] U.S. Cl. .................................. 560/263; 260/409; 260/410.6; 260/413; 560/105; 560/106; 560/265; 562/493; 562/496; 562/606; 562/607; 568/484

[58] Field of Search ...................... 560/263, 106, 105; 562/606, 607, 493, 496; 260/410.6, 409, 413

[56] References Cited

U.S. PATENT DOCUMENTS 3,579,566  5/1971  Fenton ............................... 560/263
4,221,918  9/1980  Suzuki ............................... 560/263

FOREIGN PATENT DOCUMENTS 2016061 11/1970 Fed. Rep. of Germany ...... 560/263

Primary Examiner—Vivian Garner
Attorney, Agent, or Firm—Harold N. Wells

[57] ABSTRACT

Carboxylic acid anhydrides are reacted with hydrogen to produce alkylidene diesters with high yield and with ratios of alkylidene diesters and co-product carboxylic acid near the theoretical by carrying out the reaction in the presence of a cobalt carbonyl.

5 Claims, No Drawings

PROCESS FOR CONVERSION OF ACID ANHYDRIDES TO ALKYLIDENE DIESTERS

This is a continuation of application Ser. No. 171,064, filed July 22, 1980, now abandoned.

This invention relates to the preparation of alkylidene diesters and more particularly relates to the preparation of ethylidene diacetate by the action of hydrogen on acetic anhydride.

Ethylidene diacetate is a chemical intermediate of prime commercial interest in view of its ready convertibility to a number of different tonnage chemicals of commerce. By one known conversion technique, ethylidene diacetate is readily transformed to vinyl acetate plus acetic acid; see Kirk-Othmer "*Encyclopedia of Chemical Technology*," (2nd ed.), vol. 21, page 321, Interscience, New York (1970). By another well-known conversion process, ethylidene diacetate can be transformed into acetic anhydride plus acetaldehyde; see Kirk-Othmer "*Encyclopedia of Chemical Technology*," (2nd ed.), vol. 8, pages 410–413, Interscience, New York (1965). Reference is also made to U.S. Pat. No. 2,425,389 as indicative of the flexibility of ethylidene diacetate as a chemical intermediate.

Various processes have been proposed for the preparation of ethylidene diacetate. One such process involves the reaction of acetaldehyde and acetic anhydride, the ethylidene diacetate being produced as an intermediate in the preparation of vinyl acetate, a process which has been employed to a limited extent on a commercial scale; see "Hydrocarbon Process" 44 (11), 287 (1965). British Pat. No. 1,538,782 discloses another technique for producing ethylidene diacetate which employs the carbonylation of methyl acetate or dimethyl ether in the presence of hydrogen. Fenton U.S. Pat. No. 3,579,566 treats organic acid anhydrides such as acetic anhydride with hydrogen in the presence of a catalyst comprising a complex of a Group VIII noble metal with a biphyllic ligand from the group consisting of trihydrocarbyl phosphines, arsines and stibines. The Fenton examples show the preparation of ethylidene diacetate from acetic anhydride by this technique.

The Fenton examples, however, show that the quantity of ethylidene diacetate which is produced is relatively small in relation to the theoretical quantity producible from the acetic anhydride employed. While Fenton illustrates his generic process in terms of the following "shorthand" equation:

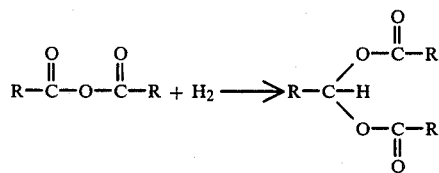

the complete equation is as follows:

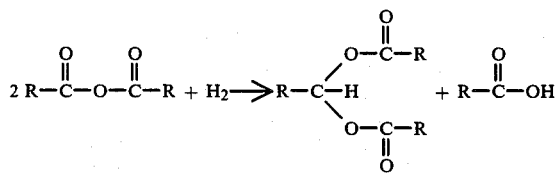

In the foregoing equation, when R is —CH$_3$ the treatment of acetic anhydride with hydrogen is illustrated. In other words, in such a reaction, one molecule of acetic acid is formed for each molecule of ethylidene diacetate produced. Competing reactions tend to form other products such as acetaldehyde and ethyl acetate, to the detriment of the yield of ethylidene diacetate.

Belgian Pat. No. 879,178 converts carboxylic acid anhydrides to 1,1-diesters with hydrogen in the presence of certain supported metals, including metals of Group VIII of the Periodic Table, and in the presence of a strong protonic acid such as hydrochloric and hydrofluoric acids. The examples show substantial carboxylic acid formation.

It is accordingly an object of this invention to provide an improved process for the preparation of alkylidene diesters, e.g., ethylidene diacetate, from carboxylic acid anhydrides, e.g., acetic anhydride, wherein increased proportions of alkylidene diesters in relation to carboxylic acid can be realized and the formation of other by-products can be minimized, i.e., the ratio of alkylidene diester, e.g., ethylidene diacetate to carboxylic acid, e.g., acetic acid, and the yields of the diester product, are high.

It is a further object of the invention to provide an improved process for the production of alkylidene diesters from carboxylic acid anhydrides which does not require the use of Group VIII noble metals.

In accordance with the invention, these and other objects are realized by the reaction of a carboxylic acid anhydride, e.g., acetic anhydride, with hydrogen in the presence of a cobalt carbonyl. It has been surprisingly discovered that a cobalt carbonyl very effectively catalyzes the reaction and does not require the presence of a promoter or ligand as in the case of the process disclosed by Fenton, in addition to not requiring the presence of a Group VIII noble metal. It also does not require the presence of an acid of any kind. Although the presence of an acid may promote the formation of by-products and complicate product separation, an acid can be tolerated, if desired, but the absence of an acid such as used in Belgian Pat. No. 879,178, is preferred.

Thus, in accordance with the invention, hydrogen is reacted with an acid anhydride in the presence of a cobalt carbonyl such as dicobalt octacarbonyl [Co(CO)$_4$]$_2$ or tetracobalt dodecacarbonyl [Co(CO)$_3$]$_4$, although any other cobalt carbonyl can also be used. Thus, ethylidene diacetate can be effectively prepared in a representative case by subjecting acetic anhydride to reaction with hydrogen in the presence of dicobalt octacarbonyl. In all cases, the reaction is carried out under anhydrous conditions.

In carrying out the process of the invention, a wide range of temperatures, e.g., 10° to 250° C. are suitable, but temperatures of 50° to 150° C. are preferably employed and the more preferred temperatures generally lie in the range of 70° to 120° C. Temperatures lower than those mentioned can be used but they tend to lead to reduced reaction rates, and higher temperatures may also be employed but there is no particular advantage in their use. Preferably the reaction is carried out at a substantially constant temperature.

The time of reaction is also not a parameter of the process and depends largely upon the temperature employed, but typical reaction or residence times, by way of example, will generally fall in the range of 0.1 to 6 hours. The reaction is preferably carried out under super-atmospheric pressures but excessively high pressures, which require special high-pressure equipment, are not necessary. In general, the reaction is effectively carried out by employing a hydrogen partial pressure which is preferably 50 to 2,000 p.s.i., and most preferably 300 to 1,000 p.s.i., although hydrogen partial pressures of 1 to 10,000 p.s.i. can also be employed. In the usual case, pressures below about 2,000 psi are generally used. By maintaining the partial pressure of hydrogen at the values specified, adequate amounts of this reactant are always present. The total pressure is preferably that required to maintain the liquid phase and, in this case, the reaction can be advantageously carried out in an autoclave or similar apparatus.

At the end of the desired residence time, the reaction mixture is separated into its several constituents, as by distillation. Preferably, the reaction product is introduced into a distillation zone, which may be a fractional distillation column, or a series of columns, effective to separate the unreacted acetic anhydride, acetic acid, other by-products, from the product ethylidene diacetate. The cobalt carbonyl is recycled.

The hydrogen is preferably employed in substantially pure form, as available commercially, but inert diluents such as carbon monoxide, carbon dioxide, nitrogen, methane, and noble gases can be present if desired. The presence of inert diluents does not affect the reaction but their presence makes it necessary to increase the total pressure in order to maintain the desired hydrogen partial pressure. The hydrogen, like other reactants should, however, be essentially dry, i.e., the hydrogen and the other reactants should be reasonably free from water. The presence of minor amounts of water such as may be found in the commercial forms of the reactants is, however, entirely acceptable.

As previously mentioned, the presence of gaseous diluents such as carbon monoxide increases the overall pressure required to provide the desired hydrogen partial pressure but the presence of carbon monoxide can be effective to maintain the catalyst for prolonged periods of time. Cobalt carbonyl has a tendency to decompose in response to elevation of temperature but it has been found that such decomposition is minimized and even completely surpressed when the temperature is maintained below 100° C. under the pressure conditions specified above. The presence of carbon monoxide provides further insurance against catalyst decomposition.

The amount of cobalt carbonyl is in no way critical and is not a parameter of the process of the invention and can vary over a wide range. As is well known to persons skilled in the art, the amount of catalyst used is that which will provide the desired suitable and reasonable reaction rate since reaction is influenced by the amount of catalyst. However, essentially any amount of catalyst will facilitate the reaction. Typically, however, the cobalt catalyst is employed in the amount of 1 mol per 1 to 100,000 mols of carboxylic acid anhydride, preferably 1 mol per 10 to 10,000 mols of carboxylic acid anhydride and most preferably 1 mol per 50 to 5,000 mols of carboxylic acid anhydride.

The anhydrides which can be used in carrying out the process of the invention are anhydrides of carboxylic acids having up to 10 carbon atoms, preferably lower alkanoic acids having up to 6 carbon atoms. These anhydrides can be represented by the formula:

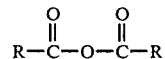

wherein R is a hydrocarbyl radical which can be an alkyl group or a monocyclic aryl group. Representative anhydrides include acetic anhydride, propionic anhydride, valeric anhydride, caprylic anhydride, benzoic anhydride, and the like. Acetic anhydride is preferred.

The process of this invention can be carried out in the presence of a solvent or diluent, if desired. Ordinarily, a solvent is not required. The solvent or diluent can be any organic solvent which is inert in the environment of the process, such as hydrocarbons, e.g., octane, benzene, toluene, xylene and tetralin, or halogenated hydrocarbons such as the chlorobenzenes, e.g., trichlorobenzene, or carboxylic acids, e.g., those containing up to 16 carbon atoms such as acetic acid, or esters such as methyl acetate and cellosolve acetate, and the like. Preferred solvents are halogenated hydrocarbons, chlorobenzenes and high boiling esters. Mixtures of solvents can also be used, such as mixtures of the solvents named above. In general, chlorobenzenes have been found to be the most suitable for use when a solvent is employed in the process. A solvent or diluent is suitably selected which has a boiling point sufficiently different from the other components in the reaction mixture that it can be readily separated by distillation, as will be readily apparent to persons skilled in the art.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of alkylidene diester, with the other organic components being recycled and, in the case of liquid-phase reaction, a residual catalyst containing fraction also being recycled.

It will be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, the catalyst components may be supported, i.e., they may be dispersed on a carrier of conventional type such as alumina, silica, silicon carbide, zirconia, carbon, bauxite, attapulgus clay, solid organic polymers, e.g., polyvinyl pyridine and polystyrene, and the like. The catalyst components can be applied to the carriers in conventional manner, e.g., by impregnation of the carrier with a solution of the catalyst, or the catalyst mixture, followed by drying. Catalyst component concentrations upon the carrier may vary widely, e.g., 0.01 weight percent to 10 weight percent, or higher. The supported catalyst is in the active form if it has a hydride or carbonyl substituent on the supported cobalt. Typical operating conditions for vapor-phase operation are a temperature of 50° to 300° C., preferably 70° to 250° C. and most preferably 100° to 200° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP).

The following examples will serve to provide a fuller understanding of the invention, but it is to be understood that they are given for illustrative purposes only, and are not to be construed as limitative of the invention. In the examples, all parts are by weight and percentages are on a molar basis, unless otherwise indicated.

EXAMPLE 1

In this example, a magnetically-stirred Hastelloy Parr bomb with a glass liner is employed as the reaction vessel. The bomb is charged with 2 parts of dicobalt octacarbonyl as catalyst, then with 40 parts of acetic anhydride, is swept out with argon and pressured to 700 p.s.i.g. with hydrogen. The bomb is then placed in an oil bath at room temperature and brought up to 100° C. in about 15 minutes. The pressure is maintained at 1,450 p.s.i.g. by recharging $H_2$ when needed. The reaction is then carried out at this constant temperature for 3 hours, whereupon the bomb is cooled to approximately room temperature, vented and opened. G.C. (gas chromatography) analysis of the reaction mixture shows it to contain 13 parts of ethylidene diacetate and 12.1 parts acetic anhydride along with 7.4 parts of acetic acid and trace levels of ethyl acetate and acetaldehyde by-products. The yield of ethylidene diacetate is 65% and the ratio of ethylidene diacetate to acetic acid is 72% of theoretical.

EXAMPLE 2

A Parr bomb as described in Example 1 is charged with 2 parts of dicobalt octacarbonyl as catalyst, then with 40 parts of acetic anhydride, is swept out with argon and pressured to 400 psig with hydrogen. The bomb is then placed in an oil bath at room temperature and brought up to 100° C. in about 15 minutes. The pressure is maintained at 1,200 p.s.i.g. by recharging $H_2$ when needed. The reaction is then carried out at this constant temperature for 3 hours, whereupon the bomb is cooled to approximately room temperature, vented and cooled. Gas chromatography analysis of the reaction mixture shows it to contain 10.3 parts of ethylidene diacetate and 22.7 parts acetic anhydride along with 5.9 parts of acetic acid and trace levels of ethyl acetate and acetaldehyde by-products. The yield of ethylidene diacetate is 84% and the ratio of ethylidene diacetate to acetic acid is 72% of theoretical.

EXAMPLE 3

A reaction vessel as described in Example 1 is charged with 1 part of tetra cobalt dodecacarbonyl as catalyst, then with 20 parts of acetic anhydride, is swept out with argon and pressured to 150 p.s.i.g. with CO and then to 1,000 p.s.i.g. with hydrogen. The bomb is then placed in an oil bath at room temperature and brought up to 100° C. in about 15 minutes. The pressure is maintained at 1,000 p.s.i.g. with hydrogen. The reaction is then carried out at this constant temperature for 3 hours, whereupon the bomb is cooled to approximately room temperature, vented and opened. Gas chromatography analysis of the reaction mixture shows it to contain 8.2 parts of ethylidene diacetate and 7.4 parts acetic anhydride along with 3.6 parts of acetic acid and trace levels of ethyl acetate and acetaldehyde byproducts. The yield of ethylidene diacetate is 91% and the ratio of ethylidene diacetate to acetic acid is 93.3% of theoretical.

EXAMPLE 4

In this Example and in the following examples, a stirred autoclave is used as the reaction vessel. The autoclave is charged with 4.1 parts of dicobalt octacarbonyl as catalyst and 400.4 parts acetic anhydride and pressured with 350 p.s.i.g. carbon monoxide and 1,150 p.s.i.g. hydrogen. The vessel is then heated up to 90° C. in about 15 minutes. During the heating period, there is absorption of gas and the pressure falls in spite of the increased temperature. The pressure is returned to 1,500 p.s.i.g. with hydrogen and is maintained at this pressure and temperature for 6 hours. G.C. analysis of the reaction mixture shows it to contain 178.6 parts of ethylidene diacetate and 134.9 parts acetic anhydride along with 84.8 parts of acetic acid, 4 parts acetaldehyde and trace levels of ethyl acetate by-product. The yield of ethylidene diacetate is 94, and the ratio of ethylidene diacetate to acetic acid is 86.6% of theoretical. The ratio of ethylidene diacetate plus acetaldehyde to acetic acid is 93% of theoretical.

EXAMPLE 5

The reaction vessel is charged with 2.1 parts of dicobalt octacarbonyl, 5 parts p-toluene sulfonic acid and 400 parts acetic anhydride and pressured with 500 p.s.i.g. carbon monoxide and 1,150 p.s.i.g. hydrogen. The vessel is then heated up to 100° C. in about 15 minutes. The pressure is returned to 1,500 p.s.i.g. with hydrogen and is maintained at this pressure and temperature for 4 hours. Gas chromatography analysis of the reaction mixture shows it to contain 83 parts of ethylidene diacetate and 282 parts acetic anhydride along with 36 parts of acetic acid and trace levels of ethyl acetate and acetaldehyde by-products. The yield of ethylidene diacetate is 98% and the ratio of ethylidene diacetate to acetic acid is 95% of theoretical.

EXAMPLE 6

The autoclave is charged with 2 parts of dicobalt octacarbonyl as catalyst and 400 parts acetic anhydride and pressured to 200 p.s.i.g. carbon monoxide and 1,300 p.s.i.g. hydrogen. The vessel is then heated up to 90° C. in about 20 minutes. The pressure is returned to 1,500 p.s.i.g. with hydrogen and is maintained at this pressure and temperature for 6 hours. Gas chromatography analysis of the reaction mixture shows it to contain 103.6 parts of ethylidene diacetate and 253 parts acetic anhydride along with 44.3 parts of acetic acid and trace levels of ethyl acetate and acetaldehyde by-products. The yield of ethylidene diacetate is 98.5 and the ratio of ethylidene diacetate to acetic acid is 96.1% of theoretical.

EXAMPLE 7

Into the reaction vessel are charged 4 parts of dicobalt octacarbonyl as catalyst and 400 parts acetic anhydride and the vessel is pressured with 130 p.s.i.g. carbon monoxide and 870 p.s.i.g. hydrogen. The vessel is then heated up to 90° C. in about 15 minutes. The pressure is returned to 1,000 p.s.i.g. with hydrogen and is maintained at this pressure and temperature for 1 hour. Gas chromatography analysis of the reaction mixture shows it to contain 74 parts of ethylidene diacetate and 296.6 parts acetic anhydride along with 30 parts of acetic acid and trace levels of ethyl acetate and acetaldehyde by-products. The yield of ethylidene diacetate is 100% and the ratio of ethylidene diacetate to acetic acid is 100% of theoretical.

EXAMPLE 8

Into the autoclave are charged 4.0 parts of dicobalt octacarbonyl as catalyst and 400 parts acetic anhydride and the vessel is pressured with 750 p.s.i.g. carbon monoxide and 750 p.s.i.g. hydrogen. The vessel is then heated up to 90° C. in about 15 minutes. The pressure is returned to 1,500 p.s.i.g. with hydrogen and is maintained at this pressure and temperature for 7 hours. Gas chromatography analysis of the reaction mixture shows it to contain 141.8 parts of ethylidene diacetate and 205.2 parts acetic anhydride along with 58.5 parts of acetic acid and trace levels of ethyl acetate and acetaldehyde by-products. The yield of ethylidene diacetate is 100% and the ratio of ethylidene diacetate to acetic acid is 99.6% of theoretical.

EXAMPLE 9

The stirred pressure vessel is charged with 4.0 parts of dicobalt octacarbonyl as catalyst and 400 parts acetic anhydride and pressured with 350 p.s.i.g. carbon monoxide and 1,150 p.s.i.g. hydrogen. The vessel is then heated up to 100° C. in about 15 minutes. The pressure is returned to 1,500 p.s.i.g. with hydrogen and is maintained at this pressure and temperature for 2 hours. Gas chromatography analysis of the reaction mixture shows it to contain 97.6 parts of ethylidene diacetate and 263.3 parts acetic anhydride along with 40.1 parts of acetic acid and trace levels of ethyl acetate and acetaldehyde by-products. The yield of ethylidene diacetate is 99.8% and the ratio of ethylidene diacetate to acetic acid is 100% of theoretical.

EXAMPLE 10

The stirred pressure vessel is charged with 20 parts of dicobalt octacarbonyl as catalyst and 400 parts acetic anhydride and pressured with 400 p.s.i. carbon monoxide. The vessel is then heated up to 100° C. in about 15 minutes. The pressure is increased to 1,200 p.s.i.g. with hydrogen and is maintained at this pressure and temperature for 7 hours. Gas chromatography analysis of the reaction mixture shows it to contain 197 parts of ethylidene diacetate and 22.4 parts acetic anhydride along with 119.8 parts of acetic acid and 17.1 parts acetaldehyde and trace levels on ethyl acetate by-product. The yield of ethylidene diacetate is 73% and the ratio of ethylidene diacetate to acetic acid is 68% of theoretical. The ratio of ethylidene diacetate and acetaldehyde to acetic acid is 87% of theoretical.

EXAMPLE 11

The reaction vessel is charged with 20 parts of dicobalt octacarbonyl as catalyst, 12 parts acetic acid and 388 parts acetic anhydride and pressured with 200 p.s.i. carbon monoxide and 700 p.s.i. hydrogen. The vessel is then heated up to 100° C. in about 30 minutes. The pressure is increased to 1,000 p.s.i.g. with hydrogen and is maintained at this pressure and temperature for 2 hours. Gas chromatography analysis of the reaction mixture shows it to contain 153.5 parts of ethylidene diacetate and 198.9 parts acetic anhydride along with 88.3 parts of acetic acid, 2.4 parts acetaldehyde and trace levels on ethyl acetate by-product. The yield of ethylidene diacetate is 95.7% and the ratio of ethylidene diacetate to acetic acid is 83% of theoretical. The ratio of ethylidene diacetate plus acetaldehyde to acetic acid is 87% of theoretical.

EXAMPLE 12

A reaction vessel as described in Example 1, is charged with 1 part of tetra cobalt dodecarbonyl as catalyst, then with 20 parts of propionic anhydride and the reaction is carried out as described in Example 3, producing results comparable to those obtained in Example 3, except that propionic acid and the corresponding alkylidene diester are produced.

EXAMPLE 13

Example 12 is repeated but there are employed 20 parts of valeric anhydride, and similar results are obtained, except that valeric acid and the corresponding alkylidene diester are produced.

EXAMPLE 14

Example 12 is again repeated but the propionic anhydride is replaced by 20 parts benzoic anhydride. Again, results comparable to those obtained in Example 3 are realized, except that benzoic acid and the corresponding alkylidene diester are produced.

What is claimed is:

1. A process for the preparation of an alkylidene diester from a carboxylic acid anhydride, which comprises reacting said carboxylic acid anhydride with hydrogen in the presence of a cobalt carbonyl, said reacting being carried out at a temperature below 100° C., whereby decomposition of said cobalt carbonyl is minimized and said alkylidene diester is produced with minimum formation of aldehydes and like by-products, and recovering the thus-produced alkylidene diester from the resulting substantially aldehyde-free reaction mixture.

2. A process as defined in claim 1, wherein the cobalt carbonyl is dicobalt octacarbonyl.

3. A process as defined in claim 1, wherein the cobalt carbonyl is tetracobalt dodecacarbonyl.

4. A process as defined in claim 1, wherein the reacting is carried out in the presence of carbon monoxide.

5. A process as defined in claim 1, wherein the acid anhydride is acetic anhydride and the alkylidene diester is ethylidene diacetate.

* * * * *